United States Patent
Senthilkumar et al.

(10) Patent No.: US 7,667,034 B2
(45) Date of Patent: Feb. 23, 2010

(54) CHEMICAL SYNTHESIS OF S-ADENOSYL-L-METHIONINE WITH ENRICHMENT OF (S,S)-ISOMER

(75) Inventors: Udayampalayam Palanisamy Senthilkumar, Chennai (IN); Ramar Padmanabhan, Chennai (IN); Venugopal Sivasankaran, Chennai (IN); Singaravel Mohan, Chennai (IN)

(73) Assignee: Orchid Chemicals & Pharmaceuticals Limited, Chennai (IN)

( * ) Notice: Subject to any disclaimer, the term of this patent is extended or adjusted under 35 U.S.C. 154(b) by 595 days.

(21) Appl. No.: 11/630,622

(22) PCT Filed: Jun. 22, 2005

(86) PCT No.: PCT/IB2005/001762

§ 371 (c)(1),
(2), (4) Date: Dec. 22, 2006

(87) PCT Pub. No.: WO2006/000883

PCT Pub. Date: Jan. 5, 2006

(65) Prior Publication Data

US 2008/0103303 A1  May 1, 2008

(30) Foreign Application Priority Data

Jun. 23, 2004  (IN) .......................... 598/CHE/2004

(51) Int. Cl.
*C07H 19/16* (2006.01)
(52) U.S. Cl. .................................. 536/26.71; 536/27.31

(58) Field of Classification Search ........................ None
See application file for complete search history.

(56) References Cited

U.S. PATENT DOCUMENTS

| | | | | |
|---|---|---|---|---|
| 6,649,753 B2 * | 11/2003 | Deshpande et al. | ...... | 536/27.31 |
| 6,881,837 B2 * | 4/2005 | Deshpande et al. | ...... | 536/27.31 |

FOREIGN PATENT DOCUMENTS

| | | |
|---|---|---|
| CA | 1057681 | 7/1979 |
| DE | 25 30 898 | 1/1976 |
| JP | A 47-37038 | 11/1972 |
| JP | B 48-44491 | 6/1973 |
| JP | A 50-92288 | 7/1975 |
| JP | A 53-5399 | 2/1978 |
| JP | A 54-154774 | 12/1979 |
| JP | A 56-99499 | 8/1981 |
| JP | A 57-086297 | 5/1982 |
| JP | A 57-086298 | 5/1982 |
| JP | A 57-099199 | 6/1982 |
| JP | A 58-036397 | 3/1983 |
| JP | A 60-70097 | 4/1985 |

OTHER PUBLICATIONS

Campbell P., "Biotechnology and Applied Biochemistry," Feb. 1987, Academic Press, Inc., vol. 9, No. 1.
"The International Journal of Biochemistry & Cell Biology," Apr. 2000, vol. 32, No. 4.

* cited by examiner

*Primary Examiner*—Traviss C McIntosh, III
(74) *Attorney, Agent, or Firm*—Oliff & Berridge, PLC

(57) ABSTRACT

This invention relates to an improved process for the industrial manufacture of S-adenosyl-L-methionine (SAMe) of formula (I), which consists of stereo-selective methylation of S-adenosyl-L-homocysteine (SAH) with the enrichment of active (S,S)-isomer.

7 Claims, No Drawings

CHEMICAL SYNTHESIS OF S-ADENOSYL-L-METHIONINE WITH ENRICHMENT OF (S,S)-ISOMER

FIELD OF THE INVENTION

This invention relates to an improved process for the industrial manufacture of S-adenosyl-L-methionine (SAMe), which consists of stereo-selective methylation of S-adenosyl-L-homocysteine (SAH) with the enrichment of active (S,S)-isomer.

BACKGROUND OF THE INVENTION

S-Adenosyl-L-methionine, known as SAMe, is the main biological donor of methyl groups and it has several important therapeutic applications. As a substance existing in the living body, SAMe has been found to possess various pharmacological actions such as improvement of energy state of ischemic brain, improvement of cerebral energy metabolism and acidosis of the model with recirculated blood flow following ischemia, etc. Variety of other functions such as inhibition of neuronal death following ischemia, improvement of cerebral glucose utility, inhibition of brain edema, improvement of EEG, improvement of evoked potential, amebiorative action on motor function, and therefore reported to be important as a cure for stroke. SAMe as an antioxidant, use for osteoarthritis, liver protection and to control aging in elderly people is also suggested SAMe is an important molecule in normal cell function and its survival. SAMe is utilized by three key metabolic pathways: trans-methylation, trans-sulfuration and polyamine synthesis. In transmethylation reactions, the methyl group of SAMe is donated to a large variety of acceptor substrates including DNA, phospholipids and proteins. In trans-sulfuration, the sulfuration of SAMe is converted via a series of enzymic steps to cysteine, a precursor of taurine and glutathione, a major cellular anti-oxidant. Given the importance of SAMe in tissue function, it is not surprising that this molecule is being investigated as a possible therapeutic agent for the treatment of various clinical disorders as mentioned in Int. J. Biochem. Cell Biol. (2000), 32(4), 391-395.

There are numerous methods known to prepare SAMe at various scales and all are enzymatic and fermentation based. JP 58036397, JP 60070097, JP 56099499 and JP 54154774 describe the preparation of S-adenosyl-L-methionine using yeast. In this process the yeast extract was adsorbed on the resin and SAMe was eluted using suitable acids. The dilute solution of the product is concentrated using reverse osmosis and the product was isolated by spray-drying. Alternatively in RO 63045, CA 1057681 and DE 2530898, use of picrolinic acid was suggested for the product isolation from the fermented mass.

Use of Saccharomyces cultured on methionine media, cells of Rhizopus pseudochinesis cultured in a medium containing methionine and the use of different cultures of various origin are reported in JP 48044491, JP 47037038, JP 53005399, and JP 50082288. Microbial production of S-adenosyl-L-methionine by reacting adenosine triphosphate (ATP) and methionine catalyzed by enzyme from yeast or other fungi and the Lactobacillus bulgaricus containing the yeast extract are described in JP 57099199, JP 57086297 and JP 57086298.

In all the above methods, enrichment of (S,S)-isomer of SAMe has been achieved; however, it is not exclusive. Normally, percentage observed for the (S,S)-isomer in the SAMe samples analyzed by HPLC method was ranging from 60% to 75%. The varying isomer ratios are attributed to the method of product isolation and the temperature at which the enzyme reaction is effected.

All the above methods have several limitations with respect to the productivity per day and require high investment. Some of the problems associated with these methods are as under:
1. Isolation of required enzyme from its natural sources is difficult and for few milligrams of enzyme a large quantity of cells is required.
2. Enzymatic synthesis of SAMe indicated the problem of product inhibition. The 5 and 10 mM reactions do not even form 1 mM of SAMe. The same is the case with immobilized enzymes. Thus, in enzymatic synthesis, non-competitive product inhibition of SAMe vs methionine leads to decrease in the rate of SAMe production at high concentration as reported in the Biotechnol. Appl. Biochem. (1987), 9(1), 39-52.
3. The product isolation is tedious and various techniques like ultra-filtration with molecular cut off, ion exchange resins columns and reverse osmosis need to be used. Thus, it requires high investment to adopt the above methods, apart from the limitations due to heavy reactor occupancy and very high dilution involved during downstream processing.

Thus the prior art teaches the production of SAMe by fermentation. While there are a few stray attempts to synthesize SAMe chemically, they have met with little success for manufacture of SAMe on commercial scale. The reason being that chemical method does not normally give the required minimum enrichment of (S,S)-isomer wherein (R,S)-isomer is 55-65% and the required (S,S)-isomer is 35-45%. The available methods produce a lot of side products owing to the presence of multiple centers in S-adenosyl-L-homocysteine susceptible to methylation.

A report by Jose R. Matos et al. published in the Biotechnol. App. Biochem. (1987), 9(1), 39-52. reveals the use of methyl iodide and trimethylsulfonium iodide (TMSI) for methylation of S-adenosyl-L-homocysteine and reports the formation of inactive isomer as a major product in a 60:40 [(R,S)-isomer:(S,S)-isomer] mole ratio. The reaction of methyl iodide was performed in 85% formic acid and was kept in dark for 3-5 days to complete. The product was isolated using Amberlite IRC-50 resin columns and lyophilized. The methylation reaction with TMSI has the disadvantage of demethylation as the concentration of dimethyl sulfide is increased in the reaction. At certain stage, reaction attains equilibrium and the formation of side product predominates. Both the methods are not useful for large scale manufacture due to its asymmetrically non-specific approach, longer reaction time, formation of side products and low yields of the required isomer. In addition, the quantum of the required isomer is much less than that obtained by the fermentation methods.

In our co-pending application we have reported the first-ever chemical process for the industrial manufacture of S-adenosyl-L-methionine with the enrichment of active (S,S)-isomer using trimethyloxonium tetrafluoroborate (TMOTFB) as a methylating agent, whose production involves the use of dimethyl ether gas, which is highly flammable gas and hence requires investment to handle in commercial scale production. Though this application teaches several methylating agent, this application is exemplified only with TMOTFB, and this application do not teach or suggest about the methylating agent of the present invention.

We have continued to our research to identify alternative methylating agent for methylation of S-adenosylhomocysteine which should be high yielding, reproducible on larger scale with the predominance of the active (S,S)-isomer and succeeded in identifying methylating agent which avoids hazardous gases like dimethyl ether.

OBJECTIVES OF THE INVENTION

The main objective of the invention is to develop a chemical approach for the stereoselective methylation of S-adenosyl-L-homocysteine (SAH) using methylating agent, which avoids hazardous gases like dimethyl ether.

Another objective of the present invention is to identify new stereo-selective methylating agents, which are safe to produce and employ in industrial level for the production of SAMe obtained is (S,S)-isomer is 58 to 75%:(R,S)-isomer is 25 to 42%.

Yet another objective of the present invention is to improve the process for the production of SAMe which is commercially viable and applicable to large scale operations which avoids biological source such as enzyme or yeast, to get desired isomer ratio.

Yet another objective is to methylate S-adenosyl-L-homocysteine to obtain SAMe with enrichment of required (S,S)-isomer.

Still another objective of the present invention is to develop an industrially feasible technique for the isolation of S-adenosyl-L-methionine from the aqueous medium wherein the use of ultra filtration with molecular cut off, ion exchange resin columns, reverse osmosis and lyophilizer are avoided.

One more embodiment of the present invention is to provide cost effective process for the preparation of oxonium salt of formula (III).

SUMMARY OF THE INVENTION

Accordingly, the invention provides a stereo-selective method for the production of SAMe, the said process comprises, reacting S-adenosyl-L-homocysteine SAH of formula (II) with methylating agent of formula (III), wherein R and $R_1$ may be identical or different and are each, independently of one another, a linear or branched alkyl radical having from 2 to 8 carbon atoms or together with the O atom to which they are bound to form a 3- to 8-membered saturated ring which may contain further hetero atoms selected from the group consisting of O and S; in the presence or absence of acid to obtain pure S-adenosyl-L-methionine of formula (I), where in the (S,S)-isomer is 58 to 75% and the (R,S)-isomer is 25 to 42%.

The reaction is shown in scheme given below:

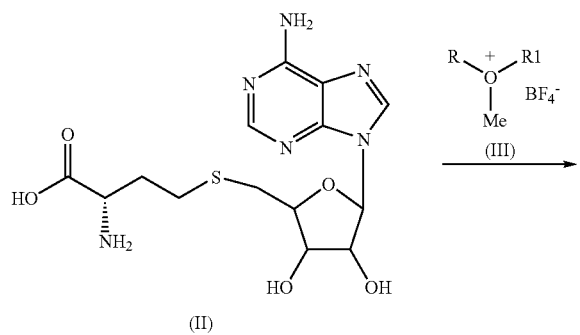

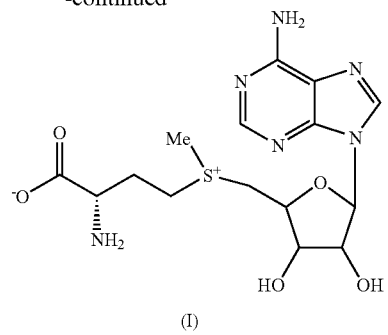

DETAILED DESCRIPTION OF THE INVENTION

In an embodiment of the present invention the compound of formula (III) used is selected from 1-methyldioxanium tetrafluoroborate, 1-methyltetrahydrofuranium tetrafluoroborate, 1-methyltetrahydro-2H-pyranium tetrafluoroborate, 1-methyloxiranium tetrafluoroborate, 1-methyloxetanium tetrafluoroborate and the like or mixtures thereof.

In an another embodiment of the present invention, the acid employed is selected from halogenated aliphatic carboxylic acid such as trifluoroacetic acid (TFA), trichloroacetic acid, tribromoacetic acid, dichlorobromoacetic acid, dichlorofluoroacetic acid, and pentachloropropionic acid; halogenated aromatic carboxylic acid such as pentachlorobenzoic acid, trichlorodifluorobenzoic acid, pentabromobenzoic acid; aliphatic or aromatic sulphonic acids such as trifluoromethanesulphonic acid, tribromomethanesulphonic acid, dichlorobromomethanesulphonic acid, dichlorofluoromethanesulphonic acid, trifluoromethanesulphonic acid, and pentachloropropanesulphonic acid; and inorganic acids such as HBr, HCl, HF, $H_2SO_4$, $HClO_4$ and $H_3PO_4$ and the like or mixtures thereof.

In yet another embodiment of the present invention, the starting material SAH of the formula (II) for the present invention is prepared according to the procedures available in the prior art.

In yet another embodiment of the present invention, the SAMe of formula (I) prepared by this invention can be converted to stable SAMe and the like according to the procedures available in the prior art.

In another embodiment of the present invention the isolation of SAMe as salts such as disulfate monotosylate, disulfate ditosylate, butanedisulfonic acid according to the procedure available in the art or by following the example given in our U.S. Pat. No. 6,881,837.

In one more embodiment, the present invention provides a process for the preparation of oxonium salts of formula (III) wherein R, $R_1$ together with the O atom to which they are bound to form a 3- to 8-membered saturated ring which may contain further hetero atoms selected from the group consisting of O and S, the said process comprising reacting compound of formula (IV), wherein X represents $CH_2$ or O or S and 'm' & 'n' may independently vary from 0 to 6 with boron trifluoride or its complex and epichlorohydrin in the presence or absence of organic solvent.

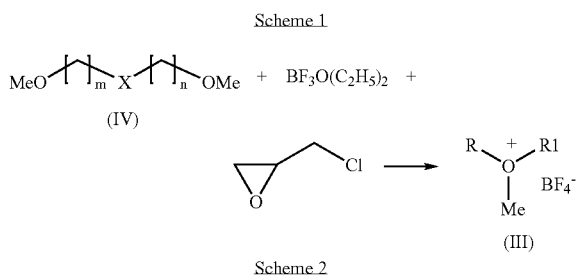

Scheme 1

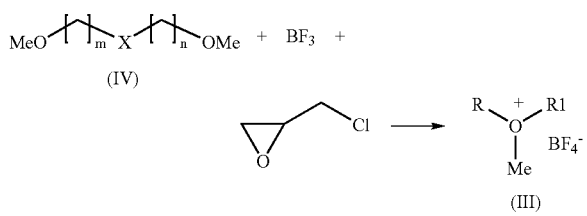

Scheme 2

In another embodiment of the present invention the compound of formula (IV) is selected from diglyme, 1,2-dimethoxyethane, 1,5-dimethoxypentane, 1,3-dimethoxypropane, 1,2-dimethoxypropane, 1,2-bis(methoxymethyl)benzene, 1,4-dimethoxybutane, and the like or mixtures thereof.

In one more embodiment of the present invention the reaction as depicted in scheme II or I can be carried out in the presence of any organic solvent, which do not affect the nature of reaction.

Many other beneficial results can be obtained by applying disclosed invention in a different manner or by modifying the invention with the scope of disclosure. The invention is further illustrated by the following examples, which should not be construed as limitations on the inventive scope embodied herein.

Example 1

Preparation of 1-methyldioxanium tetrafluoroborate by Scheme 1

To a mixture of diglyme (50 g), boron trifluoride diethyletherate (17.6 g) and dichloromethane, epichlorohydrin (13.7 g) was added slowly at below 5° C. The temperature of the reaction mixture was raised to 25° C. and stirred well. The product obtained was filtered, washed with dichloromethane, dried under vacuum to get title compound in pure form. Yield: 9.7 g Preparation of S-Adenosyl-L-Methionine Into a mixture of conc. $H_2SO_4$ (7.36 g) and trifluoroacetic acid (60 ml), S-adenosyl-L-homocysteine (10 g) was dissolved at below 0° C. Into this reaction mixture, 1-methyldioxanium tetrafluoroborate (5 g) was added and stirred well. After completion of reaction, water and anisole were added at below 0° C. Aqueous layer was separated, and added to methanol at below 0° C. Solid obtained was isolated by filtration and further dissolved in water. The clear solution was washed with dichloromethane, followed by Amberlite-LA-2 in dichloromethane solution. The aqueous layer after quantification was taken for converting salt as per conventional methods.

Preparation of S-Adenosyl-L-Methionine

Into a mixture of conc. $H_2SO_4$ (7.36 g) and trifluoroacetic acid (60 ml), S-adenosyl-L-homocysteine (10 g) was dissolved at below 0° C. Into this reaction mixture, 1-methyldioxanium tetrafluoroborate (5 g) was added and stirred well. After completion of reaction, water and diisopropyl ether were added at below 0° C. Aqueous layer was separated, and added to methanol at below 0° C. Solid obtained was isolated by filtration and further dissolved in water. The clear solution was washed with dichloromethane, followed by Amberlite-LA-2 in dichloromethane solution. The aqueous layer after quantification was taken for converting salt as per conventional methods.

Example 2

Preparation of 1-methyloxiranium tetrafluoroborate by Scheme 1

To a mixture of 1,2-dimethoxyethane (50 g), boron trifluoride diethyletherate (13.1 g) and dichloromethane, epichlorohydrin (10.2 g) was added slowly at below 5° C. The temperature of the reaction mixture was raised to 25° C. and stirred. The product obtained was filtered, washed with dichloromethane, and dried under vacuum to get title compound in pure form. Yield: 10.5 g Preparation of S-Adenosyl-L-Methionine Into a mixture of conc. $H_2SO_4$ (7.36 g) and trifluoroacetic acid (60 ml), S-adenosyl-L-homocysteine (10 g) was dissolved at below 0° C. Into this reaction mixture, 1-methyloxiranium tetrafluoroborate (6.4 g) was added and stirred till completion of reaction. After completion of reaction, and anisole were added at below 0° C. Aqueous layer was separated, and added to methanol at below 0° C. Solid obtained was separated by filtration and further dissolved in water. The clear solution washed with dichloromethane, followed by Amberlite LA2 in dichloromethane solution. The aqueous layer containing SAMe was taken for converting into its salt as per conventional methods.

Preparation of S-Adenosyl-L-Methionine

Into a mixture of conc. $H_2SO_4$ (7.36 g) and trifluoroacetic acid (60 ml), S-adenosyl-L-homocysteine (10 g) was dissolved at below 0° C. Into this reaction mixture, 1-methyloxiranium tetrafluoroborate (6.4 g) was added and stirred till completion of reaction. After completion of reaction, water and diisopropyl ether were added at below 0° C. Aqueous layer was separated, and added to methanol at below 0° C. Solid obtained was separated by filtration and further dissolved in water. The clear solution washed with dichloromethane, and then Amberlite LA2 in dichloromethane solution. The aqueous layer containing SAMe was taken for converting into its salt as per conventional methods.

Example 3

Preparation of 1-methyltetrahydro-2H-pyranium tetrafluoroborate by Scheme 1

Into a mixture of 1,5-Dimethoxypentane (10 g), boron trifluoride diethyletherate (14.6 g) and dichloromethane, epichlorohydrin (11.7 g) was added slowly at below 5° C. The reaction mixture warmed to 25° C. and stirred. The product obtained was filtered washed with dichloromethane, dried under vacuum to get titled compound in pure form. Yield: 8.8 g Preparation of S-Adenosyl-L-Methionine To Conc. H$_2$SO$_4$ (7.36 g) and trifluoroacetic acid (60 ml) S-Adenosyl-L-homocysteine (10 g) was dissolved at below 0° C. To this reaction mixture, 1-methyltetrahydro-2H-pyranium tetrafluoroborate (5.4 g) was added and stirred till completion of reaction. After completion of the reaction, water and anisole were added at below 0° C. Aqueous layer was separated, and added to methanol at below 0° C. Solid obtained was filtered and dissolved in water. The clear solution washed with dichloromethane, followed by Amberlite-LA-2 in dichloromethane solution. The aqueous layer was taken for salt preparation as per conventional methods.

Preparation of S-Adenosyl-L-Methionine

To Conc. H$_2$SO$_4$ (7.36 g) and trifluoroacetic acid (60 ml) S-Adenosyl-L-homocysteine (10 g) was dissolved at below 0° C. To this reaction mixture, 1-methyltetrahydro-2H-pyranium tetrafluoroborate (5.4 g) was added and stirred till completion of reaction. After completion of the reaction water and diisopropyl ether were added at below 0° C. Aqueous layer was separated, and added to methanol at below 0° C. Solid obtained was filtered and dissolved in water. The clear solution washed with dichloromethane, followed by Amberlite-LA-2 in dichloromethane solution. The aqueous layer was taken for salt preparation as per conventional methods.

Example 4

Preparation of 1-methyldioxanium tetrafluoroborate by Scheme 2

To a solution of diglyme (125 g) in dichloromethane, boron trifluoride gas (52.6 g) was purged at below 5° C., epichlorohydrin (86.2 g) was added slowly at below 5° C. The temperature of the reaction mixture was raised to 25° C. and stirred well. The product obtained was filtered, washed with dichloromethane, dried under vacuum to get title compound in pure form. Yield: 103 g.

Preparation of S-Adenosyl-L-Methionine

Into a mixture of conc. H$_2$SO$_4$ (7.36 g) and trifluoroacetic acid (60 ml), S-adenosyl-L-homocysteine (10 g) was dissolved at below 0° C. Into this reaction mixture, 1-methyldioxanium tetrafluoroborate (5 g) was added and stirred well. After completion of reaction, water and anisole were added at below 0° C. Aqueous layer was separated, and added to methanol at below 0° C. Solid obtained was isolated by filtration and further dissolved in water. The clear solution was washed with dichloromethane, followed by Amberlite-LA-2 in dichloromethane solution. The aqueous layer after quantification was taken for converting salt as per conventional methods.

Preparation of S-Adenosyl-L-Methionine

Into a mixture of conc. H$_2$SO$_4$ (7.36 g) and trifluoroacetic acid (60 ml), S-adenosyl-L-homocysteine (10 g) was dissolved at below 0° C. Into this reaction mixture, 1-methyldioxanium tetrafluoroborate (5 g) was added and stirred well. After completion of reaction, water and diisopropyl ether were added at below 0° C. Aqueous layer was separated, and added to methanol at below 0° C. Solid obtained was isolated by filtration and further dissolved in water. The clear solution was washed with dichloromethane, followed by Amberlite-LA-2 in dichloromethane solution. The aqueous layer after quantification was taken for converting salt as per conventional methods.

Example 5

Preparation of 1-methyloxiranium tetrafluoroborate by Scheme 2

To a solution of 1,2-dimethoxyethane (125 g) in dichloromethane, boron trifluoride, (78.4 g) gas was purged at below 5° C., epichlorohydrin (128.3 g) was added slowly at below 5° C. The temperature of the reaction mixture was raised to 25° C. and stirred. The product obtained was filtered, washed with dichloromethane (MDC), and dried under vacuum to get title compound in pure form. Yield: 122 g.

Preparation of S-Adenosyl-L-Methionine

Into a mixture of conc. H$_2$SO$_4$ (7.36 g) and trifluoroacetic acid (60 ml), S-adenosyl-L-homocysteine (10 g) was dissolved at below 0° C. Into this reaction mixture, 1-methyloxiranium tetrafluoroborate (6.4 g) was added and stirred till completion of reaction. After completion of reaction, water and anisole were added at below 0° C. Aqueous layer was separated, and added to methanol at below 0° C. Solid obtained was separated by filtration and further dissolved in water. The clear solution washed with dichloromethane, followed by Amberlite LA2 in dichloromethane solution. The aqueous layer containing SAMe was taken for converting into its salt as per conventional methods.

Preparation of S-Adenosyl-L-Methionine

Into a mixture of conc. H$_2$SO$_4$ (7.36 g) and trifluoroacetic acid (60 ml), S-adenosyl-L-homocysteine (10 g) was dissolved at below 0° C. Into this reaction mixture, 1-methyloxiranium tetrafluoroborate (6.4 g) was added and stirred till completion of reaction. After completion of reaction, water and diisopropyl ether were added at below 0° C. Aqueous layer was separated, and added to methanol at below 0° C. Solid obtained was separated by filtration and further dissolved in water. The clear solution washed with dichloromethane, followed by Amberlite LA2 in dichloromethane solution. The aqueous layer containing SAMe was taken for converting into its salt as per conventional methods.

Example 6

Preparation of 1-methyltetrahydro-2H-pyranium tetrafluoroborate by Scheme 2

Into a mixture of 1,5-Dimethoxypentane (125 g) and dichloromethane boron trifluoride gas (53.5 g) was purged at below 5° C., epichlorohydrin (87.6 g) was added slowly at below 5° C. The reaction mixture warmed to 25° C. and stirred. The product obtained was filtered washed with dichloromethane, dried under vacuum to get titled compound in pure form. Yield: 108 g.

Preparation of S-Adenosyl-L-Methionine

To Conc. H$_2$SO$_4$ (7.36 g) and trifluoroacetic acid (60 ml) S-Adenosyl-L-homocysteine (10 g) was dissolved at below 0° C. To this reaction mixture, 1-methyltetrahydro-2H-pyranium tetrafluoroborate (5.4 g) was added and stirred till completion of reaction. After completion of the reaction, water and anisole were added at below 0° C. Aqueous layer was separated, and added to methanol at below 0° C. Solid obtained was filtered and dissolved in water. The clear solution washed with dichloromethane, followed by Amberlite-LA-2 in dichloromethane solution. The aqueous layer was taken for salt preparation as per conventional methods.

Preparation of S-Adenosyl-L-Methionine

To Conc. $H_2SO_4$ (7.36 g) and trifluoroacetic acid (60 ml) S-Adenosyl-L-homocysteine (10 g) was dissolved at below 0° C. To this reaction mixture, 1-methyltetrahydro-2H-pyranium tetrafluoroborate (5.4 g) was added and stirred till completion of reaction. After completion of the reaction, water and diisopropyl ether were added at below 0° C. Aqueous layer was separated, and added to methanol at below 0° C. Solid obtained was filtered and dissolved in water. The clear solution washed with dichloromethane, followed by Amberlite-LA-2 in dichloromethane solution. The aqueous layer was taken for salt preparation as per conventional methods.

Some of the advantages of the invention and the salient features are:
1) avoids the use of trimethyloxonium tetrafluoroborate (TMOTFB) and does not liberate dimethyl ether gas while performing stereoselective methylation reaction to produce SAMe, & thus avoids the associated hazards.
2) the process of stereoselective methylation is simple and straightforward and can be implemented on manufacturing scale smoothly;
3) it does not require any biological source for enzyme or yeast, and affords consistent isomer ratio;
4) does not liberate dimethyl ether while performing stereoselective methylation reaction to produce SAMe;
5) the preparation of the methylating agent does not involve hazardous gases like dimethyl ether, and related hazards in handling such gases.

We claim:

1. A stereo-selective process for the preparation of S-adenosyl-L-methionine (SAMe) of formula (I) or its pharmaceutically acceptable salts thereof:

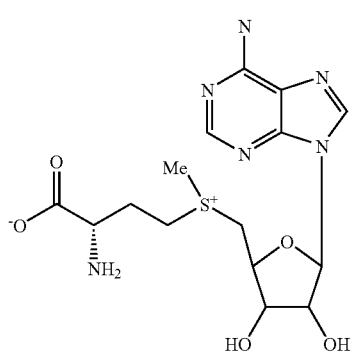

the said process comprises reacting S-adenosyl-L-homocysteine (SAH) of formula (II) or its salts with methylating agent of formula (III),

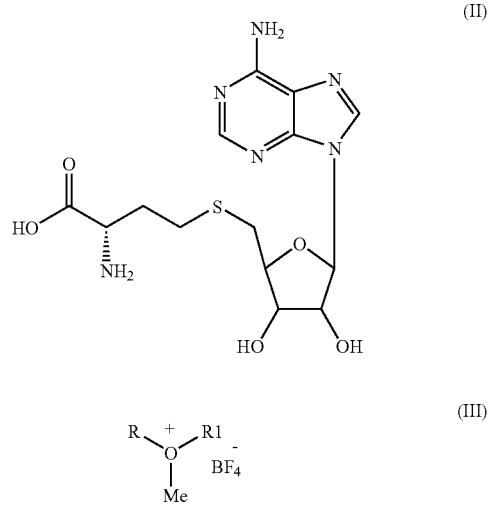

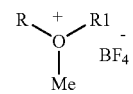

wherein R and $R_1$ may be identical or different and are each, independently of one another, a linear or branched alkyl radical having from 2 to 8 carbon atoms or together with the O atom to which they are bound to form a 3- to 8-membered saturated ring which may contain further hetero atoms selected from the group consisting of O and S; in the presence or absence of acid.

2. The process as claimed in claim 1, wherein the compound of formula (III) is selected from 1-methyldioxanium tetrafluoroborate, 1-methyltetrahydrofuranium tetrafluoroborate, 1-methyltetrahydro-2H-pyranium tetrafluoroborate, 1-methyloxiranium tetrafluoroborate, 1-methyloxetanium tetrafluoroborate or mixtures thereof.

3. The process as claimed in of claim 1, wherein the acid employed is selected from aliphatic carboxylic acid such as trifluoroacetic acid (TFA), trichloroacetic acid, tribromoacetic acid, and inorganic acids such as HBr, HCl, HF, $H_2SO_4$, $HClO_4$ and $H_3PO_4$ or mixtures thereof, preferably a mixture of Conc.$H_2SO_4$ and trifluoroacetic acid.

4. The process as claimed in of claim 1, wherein the enatiomer ratio of compound of formula (I) obtained is (S,S)-isomer is 58 to 75%:(R,S)-isomer is 25 to 42%.

5. A process for the preparation of oxonium salts of formula (III),
  i) the said process comprising reacting a compound of formula (IV),

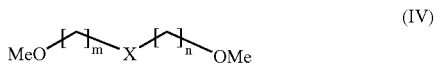

wherein X represents $CH_2$ or O or S and 'm' & 'n' may independently vary from 0 to 6 with boron trifluoride gas or its complex with epichlorohydrin in the presence or absence of an organic solvent.

6. A stereo-selective process for the preparation of S-adenosyl-L-methionine (SAMe) of formula (I) or its pharmaceutically acceptable salts thereof:

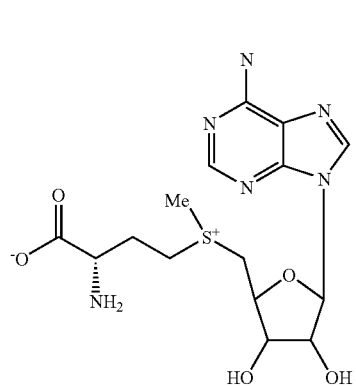
(I)

the said process comprises reacting S-adenosyl-L-homocysteine (SAH) of formula (II) or its salts with methylating agent selected from a group 1-methyldioxanium tetrafluoroborate, 1-methyltetrahydrofuranium tetrafluoroborate, 1-methyltetrahydro-2H-pyranium tetrafluoroborate, 1-methyloxiranium tetrafluoroborate, 1-methyloxetanium tetrafluoroborate or mixtures thereof

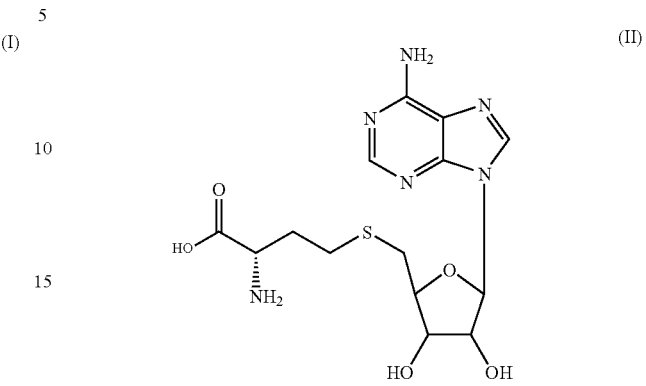
(II)

in the presence or absence of acid.

7. A method/process as claimed in claim 1, the method/process further comprising the preparation of a pharmaceutically acceptable salt using the S-adenosyl-L-methionine.

* * * * *